(12) United States Patent
Drean

(10) Patent No.: US 7,147,821 B1
(45) Date of Patent: Dec. 12, 2006

(54) TREATMENT PROCESS FOR A GASEOUS MEDIUM CONTAINING CONTAMINATING PARTICLES

(75) Inventor: Henri Louis Drean, Paris (FR)

(73) Assignee: Rasar Holding N.V., Curacao (AN)

( * ) Notice: Subject to any disclaimer, the term of this patent is extended or adjusted under 35 U.S.C. 154(b) by 0 days.

(21) Appl. No.: 09/959,444

(22) PCT Filed: Apr. 25, 2000

(86) PCT No.: PCT/FR00/01079

§ 371 (c)(1),
(2), (4) Date: Jul. 29, 2002

(87) PCT Pub. No.: WO00/64499

PCT Pub. Date: Nov. 2, 2000

(30) Foreign Application Priority Data

Apr. 27, 1999 (FR) .................................. 99 05320

(51) Int. Cl.
*A61L 9/22* (2006.01)
*B01J 19/12* (2006.01)

(52) U.S. Cl. ................ 422/4; 204/164; 204/168; 95/57

(58) Field of Classification Search ............. 96/66, 96/87, 95, 56, 223; 422/22, 28, 30, 121, 422/124, 306, 186.04, 4; 250/432 R; 55/342; 95/57, 273; 204/164, 168
See application file for complete search history.

(56) References Cited

U.S. PATENT DOCUMENTS

| | | | | |
|---|---|---|---|---|
| 2,248,618 A | * | 7/1941 | Fischer | .................. 250/437 |
| 3,201,924 A | * | 8/1965 | Fulford et al. | .................. 55/324 |
| 4,227,894 A | * | 10/1980 | Proynoff | .................. 96/58 |
| 4,313,739 A | * | 2/1982 | Douglas-Hamilton | .......... 95/79 |
| 5,445,798 A | * | 8/1995 | Ikeda et al. | .................. 422/121 |
| 5,635,394 A | * | 6/1997 | Horn | .......................... 435/266 |
| 5,667,564 A | * | 9/1997 | Weinberg | .................. 96/58 |
| 5,822,980 A | | 10/1998 | Chen | |
| 5,997,619 A | * | 12/1999 | Knuth et al. | .................. 96/224 |
| 6,118,040 A | * | 9/2000 | Coral et al. | .............. 204/157.3 |
| 6,156,103 A | * | 12/2000 | Abdel-Rahman | .............. 96/64 |

FOREIGN PATENT DOCUMENTS

JP  58076126 A  * 10/1981

OTHER PUBLICATIONS

Dictionary definition of converge The American Heritage® Dictionary of the English Language, Fourth Edition Copyright © 2004, 2000 by Houghton Mifflin Company. Published by Houghton Mifflin Company. All rights reserved.*

* cited by examiner

*Primary Examiner*—Krisanne Jastrzab
*Assistant Examiner*—Sean E. Conley
(74) *Attorney, Agent, or Firm*—Leydig, Voit & Mayer, Ltd.

(57) ABSTRACT

The invention relates to a method for treating a gaseous medium containing contaminating particles, such as microorganisms, bacteria, or viruses. The inventive method consists of generating an accelerated electron flux; the electron flux interacting with the gaseous medium, whereby the particles are broken or destroyed by ionization as a result of the interaction and the gaseous medium is sterilized. The invention can be used to treat the atmospheres of refrigerated vessels in refrigerators.

17 Claims, 3 Drawing Sheets

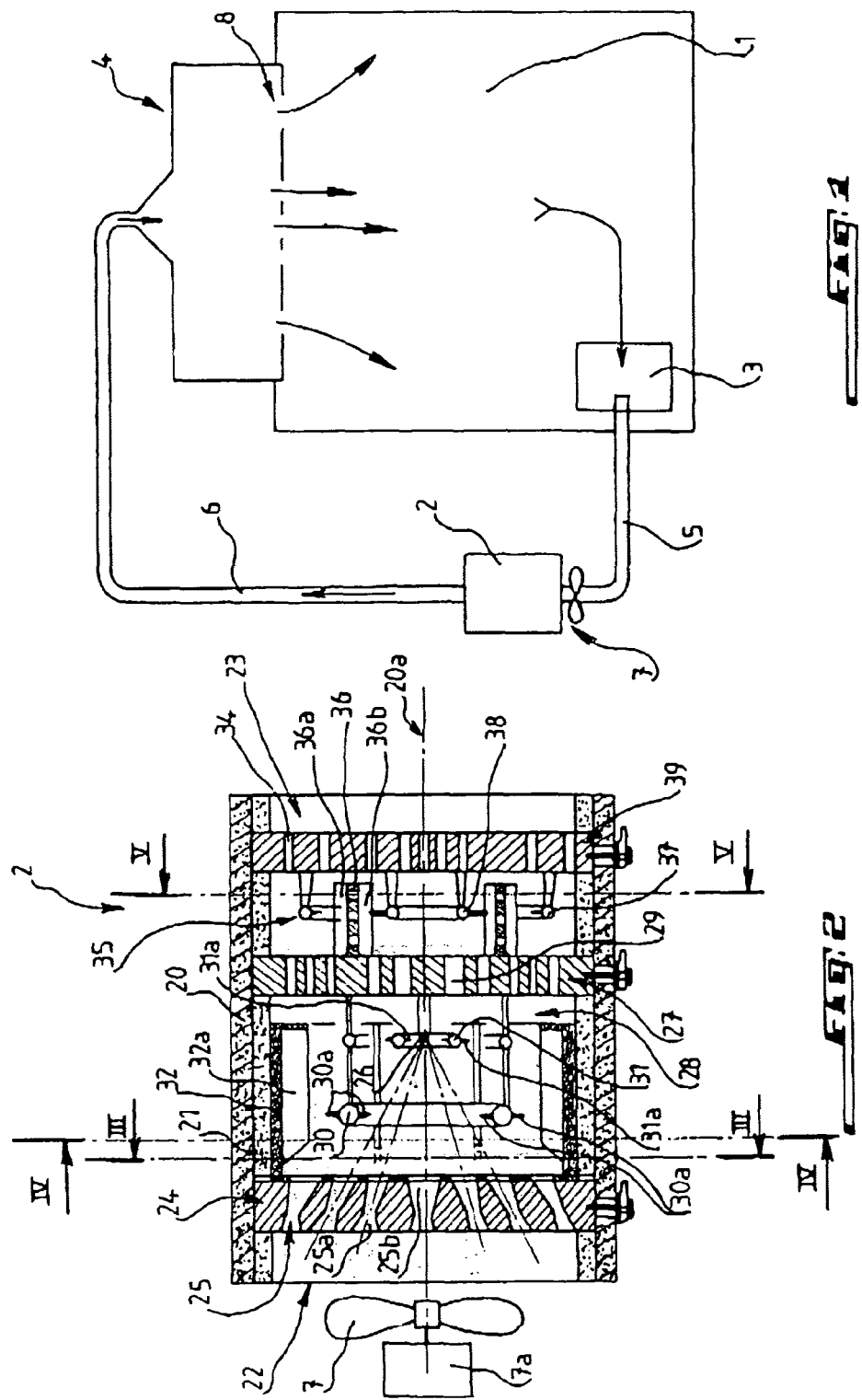

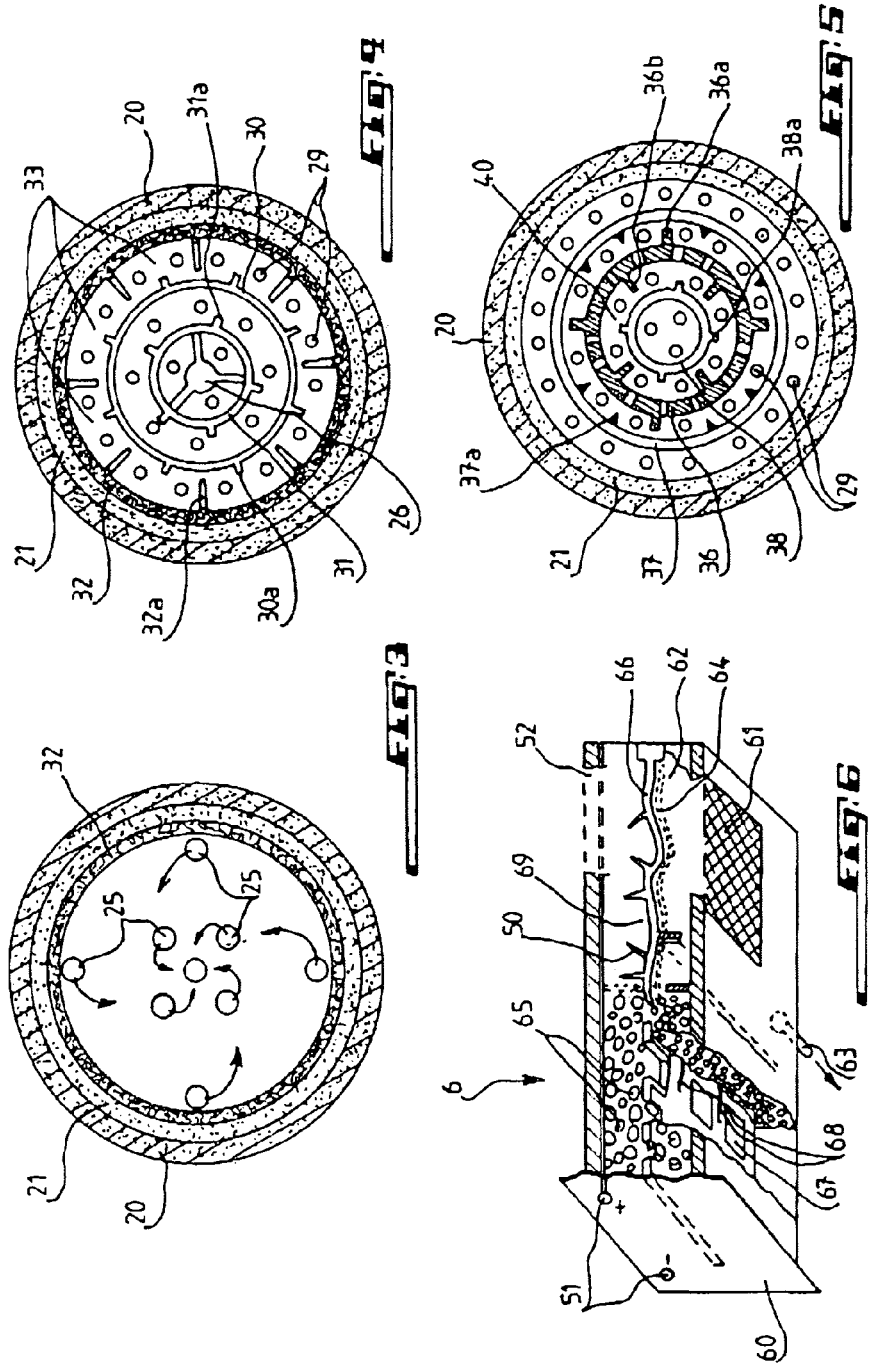

TREATMENT PROCESS FOR A GASEOUS MEDIUM CONTAINING CONTAMINATING PARTICLES

FIELD OF THE INVENTION

The present invention relates to a treatment process for a gaseous medium containing contaminating particles of the microorganism, bacteria or virus type.

This process can be used particularly for treatment of air circulating in air conditioning devices, for example, in hospitals or trains, or else for treatment of preserving atmospheres, for example, those of the refrigerated chambers of cold storage rooms or refrigerators.

The invention also relates to a device for treatment of a gaseous medium containing contaminating particles.

BACKGROUND

Known air conditioning devices allow one to regulate the temperature of the air which they treat, but have no means for eliminating possible contaminating particles present in it, which can prove very detrimental to the health of the people breathing this conditioned air.

Furthermore, the refrigerators currently in service essentially have refrigerated chambers at a positive temperature below 10° C. in order to improve preservation of living materials. However, no device is provided for treating the atmospheres surrounding these materials that are in the process of ripening and biological decomposition.

Now, the ripening of living materials generates volatile organic compounds, such as ethylene, as well as contaminating particles of the microorganism, bacteria, yeast, mildew, and virus type. Airborne dispersion of these volatile organic compounds and these contaminating particles causes microbiological alterations that generally accelerate the action of the enzymes and therefore the autocatalysis of these ripening metabolisms and the degeneration of the living materials in ripening phase, which are also influenced by the temperature, the relative humidity, the speed of circulation of the air, and the light intensity. These phenomena cause losses of organoleptic qualities of the products and losses of material, and therefore lead to significant risks of food poisoning.

SUMMARY OF THE INVENTION

The invention aims to remedy these disadvantages by proposing a treatment process for a gaseous medium containing contaminating particles that enables one to effectively control the airborne microbial contamination.

This process is well suited to the treatment of gaseous media in enclosures for preservation of living materials, particularly of food products, this process making it possible to improve their preservation significantly. The process can, however, be applied to any type of gaseous medium.

Thus, the invention relates to a treatment process for a gaseous medium containing contaminating particles, which consists of:

generating a flow of accelerated electrons, making the electron flow and the gaseous medium interact, this interaction causing the breakdown or destruction of the particles by ionization, and the sterilization of the gaseous medium.

In order to improve the effectiveness of this treatment process, the gaseous medium is accelerated and rendered convergent towards the electron flow, preferably in the form of a swirling stream, before interaction with the electron flow.

Preferably, this process consists also of generating another electron flow and of making it interact with the gaseous medium whose contaminating particles have been broken down beforehand by ionization, in order to cause the transformation of the particles into gas.

Moreover, the process according to the invention advantageously consists of running the gaseous medium through an active porous material in order to bring about the absorption of this gaseous medium that penetrates the pore spaces of the material, then the absorption of the gaseous medium in the course of which a chemical reaction occurs between the organic compounds of the gaseous medium and the material itself that transforms the volatile organic compounds into non-toxic gases, particularly $CO_2$ or $SO_2$.

In this case, the process advantageously has a step to recover water present in the gaseous medium, before this medium runs through the porous material.

In a preferred application, the process consists first of all of suctioning the gaseous medium from an enclosure, such as a refrigerator chamber, and then of delivering the gaseous medium, after treatment, back to the enclosure.

The invention also relates to a device for treatment of a gaseous medium containing contaminating particles, this device including a sterilizer with:

an envelope in which the gaseous medium is intended to circulate, comprising a first opening for entrance of the gaseous medium and a second opening for exit of the treated gaseous medium and a first plate and a second plate defining a first chamber in the envelope, the first plate being attached at the site of the first opening and having means of accelerating the gaseous medium, this electrically conductive first plate being connected to the positive potential of an electrical power supply, whereas the second plate supports at least one core placed in the first chamber and that is intended to emit electrons, the second plate being electrically conductive and connected to the negative potential of the electrical power supply.

Preferably, the second plate supports two concentric cores spaced apart, the internal core of smaller diameter being the farthest from the first plate, while the first plate is perforated with channels including a convergent section and a divergent section whose axes converge toward the center of the internal core.

Preferably, also, the device has vanes extending toward the interior of the first chamber and that are in electrical contact with the first plate, in order to define magnetic resonance cavities.

Preferably, the second plate is perforated through with holes and defines, with a third plate, a second chamber in the envelope, the second plate moreover supporting at least one electrode extending in the second chamber and the third plate being attached at the site of the second opening of the envelope and supporting at least one core extending in the second chamber in the direction of the electrode, this third plate being electrically conductive and connected to the positive potential of the electrical power supply and having holes passing through it in order to evacuate the gaseous medium from the envelope of the sterilizer.

The electrode borne by the second plate is advantageously roughly cylindrical, and has vanes on its periphery in order to form magnetic resonance cavities.

Preferably, the treatment device according to the invention has at least one filter, intended to be traversed by the gaseous medium, with a casing filled at least partially with a porous active material containing an oxidizing substance, an oxido-reducing substance, and an oxygen absorbing substance, for the conversion of volatile organic compounds into non-toxic gases, of the $CO_2$ or $SO_2$ type.

This active material advantageously contains approximately 47 to 52 wt % of a silicon and carbon composite substance, approximately 12 to 20 wt % carbon, approximately 5 to 7 wt % hydroxyl, and approximately 1 to 2 wt % oxygen, its porosity in particular being between 65 and 90% by volume.

Preferably, the filter contains a nickel plate placed inside the porous active material and that is intended to be placed under an electrical potential, this plate having windows faced with platinum sponge.

Advantageously, some means for recovering the water present in the gaseous medium is provided at the entrance of the filter.

Preferably also, the plate of the filter has electrical resistors whose temperature function can be programmed in order to ensure the recycling and regeneration of the active material.

Finally, the invention relates to a refrigerated apparatus that has at least one storage compartment associated with a treatment device according to the invention, and having means of setting the temperature, the relative humidity, and the ventilation at values suitable for the products that are intended to be placed in the compartment.

Preferably, the treatment device associated with the storage compartment has two filters, the first filter being situated at the entrance of a ventilation circuit that sucks in the gaseous medium contained in the storage compartment and delivers it to the sterilizer of the device, the second filter being situated at the outlet of the ventilation circuit and receiving the gaseous medium treated by the sterilizer in order to deliver the filtered gaseous medium to the storage compartment.

BRIEF DESCRIPTION OF THE DRAWINGS

The invention will be better understood, and other aims, advantages and characteristics of it will appear more clearly, upon reading of the following description given with reference to the appended drawings, which represent non-limiting embodiments of the invention and in which:

FIG. 1 diagrammatically illustrates an example of a treatment device according to the invention, which has two filters and a sterilizer;

FIG. 2 is an axial section of a sterilizer example;

FIG. 3 is a section along line III—III of FIG. 2;

FIG. 4 is a section along line IV—IV of FIG. 2;

FIG. 5 is a section along line V—V of FIG. 2;

FIG. 6 is a partially cut-away oblique view of an example of a filter of the device illustrated in FIG. 1;

DETAILED DESCRIPTION

Figure 8:
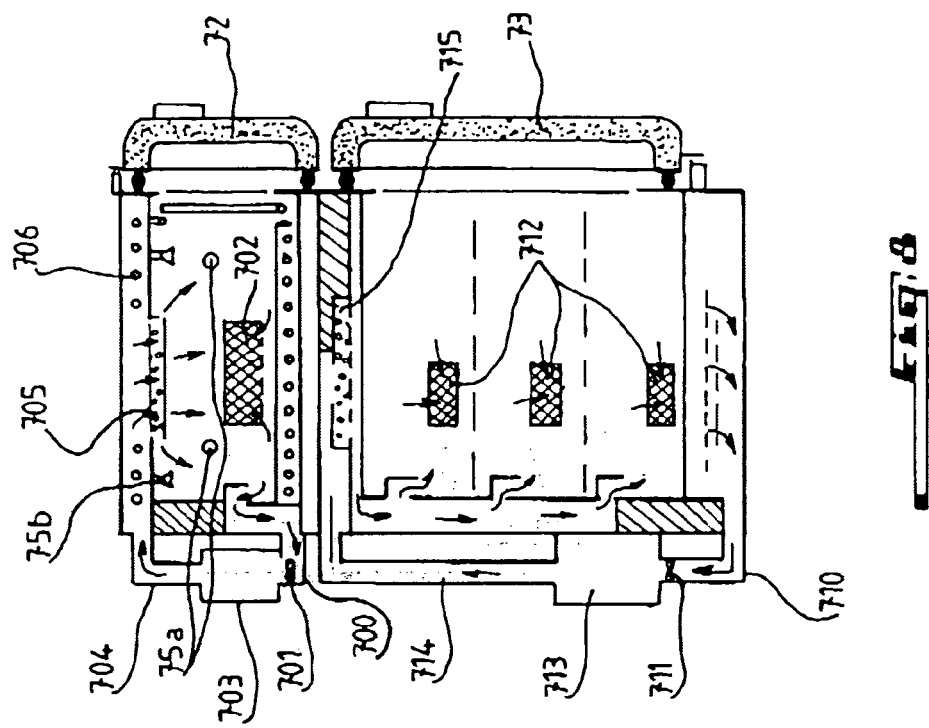
FIG. 8 is a section along line VIII—VIII of FIG. 7.
Figure 7:
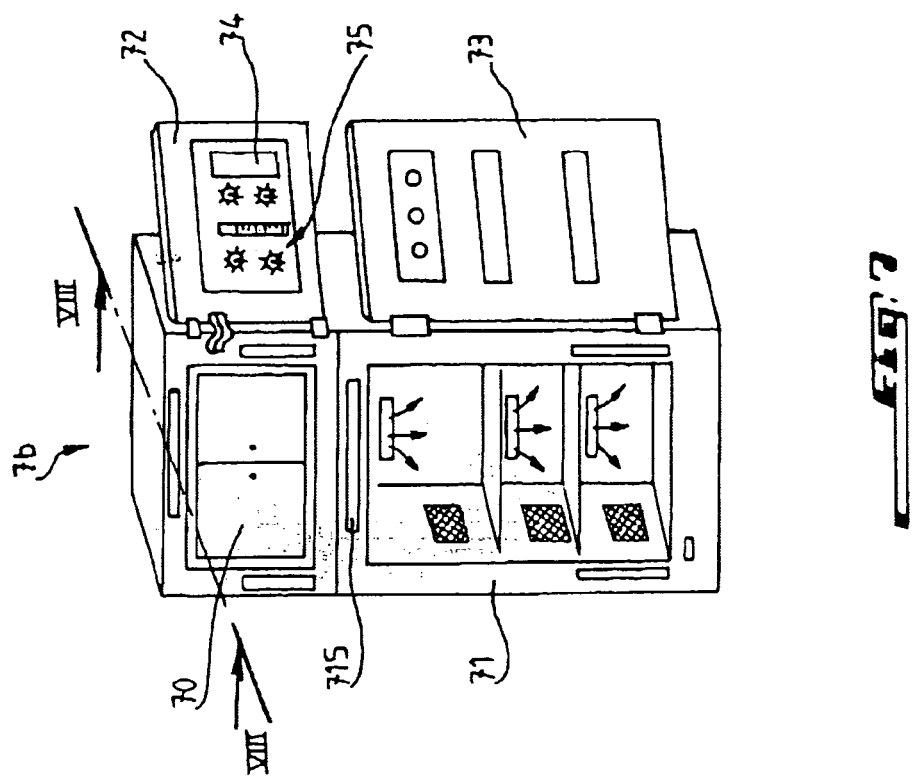
FIG. 7 is a general oblique view of a refrigerated apparatus according to the invention.

First of all, in reference to FIG. 1, the treatment device according to the invention is associated with enclosure 1 containing a gaseous medium containing contaminating particles, particularly of microorganism, bacteria, yeast, mildew, and viruses. This enclosure 1 can, in particular, be a storage chamber of a refrigerator.

The device according to the invention illustrated in FIG. 1 has sterilizer 2 and two filters 3 and 4. The essential element of this treatment device is sterilizer 2; filters 3 and 4 can be omitted.

The different elements constituting the treatment device are placed in a ventilation circuit that has two ducts, 5 and 6. Preferably, fan 7 is associated with this circuit.

Put in a simplified manner, the gaseous medium present in enclosure 1 is sucked in through filter 3 in order to be conveyed to sterilizer 2 via duct 5. The gaseous medium is then conveyed to filter 4 via duct 6.

Finally, the gaseous medium treated by the device according to the invention is reintroduced into enclosure 1, for example, through baffles 8.

Sterilizer 2 will be described in more detail with reference to FIGS. 2 to 5.

FIG. 2 represents an example of a sterilizer of the treatment device according to the invention, in axial section.

This sterilizer has envelope 20, in this case roughly cylindrical, with internal envelope 21 of a dielectric insulating material, different metallic pieces being provided inside enclosure 20 in order to make possible ionization of the contaminating particles present in the gaseous medium that is intended to circulate through sterilizer 2.

Envelope 20 has first opening 22 for entrance of the gaseous medium into sterilizer 2 and second opening 23 for exit of the gaseous medium after treatment in sterilizer 2.

Sterilizer 2 has first plate 24, made of an electrically conductive material, which is connected to the positive potential of an electrical power supply.

This first plate 24 is attached at the site of first opening 22, and it has means for accelerating the gaseous medium entering sterilizer 2.

In this embodiment, the means consist of channels 25 passing through first plate 24.

These channels are in nozzle form and have a convergent section 25a and a divergent section 25b, whose axes converge at point 26, which is situated on axis 20a of the envelope and which constitutes an electrical center.

Channels 25 have a shape such that they accelerate the gaseous flow penetrating into the sterilizer. Moreover, they are distributed in plate 24 in such a way as to create a peripheral turbulence, so that the gaseous flow circulates in the form of a swirling stream which converges towards electrical center 26. This is illustrated in FIG. 3, in which only a few channels 25 are represented.

Also provided inside envelope 20 is second plate 27 which, like first plate 24, is arranged roughly perpendicularly to axis 20a of envelope 20.

This plate 27 is produced out of an electrically conductive material and is connected to the negative potential of the electrical power supply.

Thus, first and second plates 24 and 27 define first chamber 28 in envelope 20.

Second plate 27 is drilled through with holes 29 that are roughly parallel to axis 20a of envelope 20.

This second plate 27 supports external cylindrical core 30 and internal cylindrical core 31.

Preferably, internal core 31 is a distance from second plate 27, following axis 20a, that corresponds roughly to a third of the axial distance between first and second plates 24 and 27. Similarly, external core 30 is preferably situated an axial distance from second plate 27 that corresponds roughly to two thirds of the distance between the two plates 24 and 27.

Thus, the two cores 30 and 31 extend in chamber 28 and are roughly centered on axis 20a of envelope 20. As indicated in the preceding, the orientation of nozzles 25 is such that the cone defined by the axis of the different nozzles 25 is centered on electrical center 26 corresponding to the center of internal core 31.

Also provided inside of chamber 28 is cylindrical piece 32 which is in electrical contact with first plate 24, and preferably is in contact with internal envelope 21.

This cylindrical piece 32 has, on its interior periphery, vanes 32a which extend in the interior of first chamber 28. As illustrated by FIG. 4, these vanes 32a have the function of delimiting magnetic resonance cavities 33, centered on the two cores 30 and 31, which are intended to emit high energy electrons as an effect of putting second plate 27 under high negative potential.

The elements constituting sterilizer 2 that have just been described constitute the essential elements of the sterilizer, as will be shown by its operation to be described later.

However, sterilizer 2 can also include, inside of envelope 20, third plate 39 that is roughly perpendicularly to axis 20a of the envelope and attached at the site of second opening 23.

This plate 39 is made from an electrically conductive material and is connected to the positive potential of the electrical power supply. It is perforated with holes 34 that extend roughly according to i.e., parallel to, axis 20a. These holes 34 allow the gaseous medium treated by the sterilizer to leave through second opening 23.

Second and third plates 27 and 39 define second chamber 35 of sterilizer 2.

Attached to second plate 27 is perforated cylindrical electrode 36 that extends in second chamber 35. As illustrated by FIG. 5, this electrode 36 has, on its exterior periphery, vanes 36a, and on its interior periphery, vanes 36b which define magnetic resonance cavities 40.

Furthermore, attached to third plate 39 are external core 37 and internal core 38 which, like electrode 36, are roughly centered on axis 20a of envelope 20. External core 37 has, on its inner periphery, protuberances 37a, while internal core 38 has, on its outer periphery, protuberances 38a.

The operation of sterilizer 2 is as follows.

Sterilizer 2 receives the gaseous medium to be treated that circulates inside the sterilizer, under the impetus of fan 7 driven by geared motor 7a whose speed is automatically controlled, as a function of the pressure drop existing between the flow of gaseous medium at the site of first opening 22 and at the site of second opening 23.

Advantageously, the gaseous medium entering through first opening 22 of sterilizer 2 has a speed between 20 and 80 cm/sec. Passing through nozzles 25, the gaseous medium penetrates first chamber 28 at a stabilized speed between 70 and 200 cm/sec.

Since nozzles 25 are oriented on electrical center 26, the gaseous medium circulates in a swirling stream that is treated by low energy electrons emitted by the two cores 30 and 31 attached to second plate 29.

The energy of these electrons is advantageously approximately 0.1 Mev, the electrical power supply for the sterilizer being at potentials between 20 and $30 \times 10^3$ volts.

Thus, sterilizer 2 generates a flow of accelerated electrons whose interaction with the gaseous medium loaded with contaminating particles, such as microorganisms, causes the ionization of the particles, which leads to chemical modifications and biological effects, destroying all the molecular structures of the nucleic acids and, more generally, all the constituents of the eukaryotic, prokaryotic and akaryotic cells. This interaction also causes breaking of the chains and of the hydrogen bonds, while leading to destructive oxidation of the lipoprotein structures of the membranes.

Magnetic resonance cavities 33, provided in first chamber 28, make possible the amplification of the energy of ion emission and its frequency modes, that is to say the generation of electron flows with agitation at a variable frequency linked with the state of the surrounding atmosphere. Because of this characteristic, sterilizer 2 and the process according to the invention make it possible to destroy all the microbiological constituents, regardless of their radiosensitivity. Protuberances 30a and 31a provided on the outer and inner peripheries of, respectively, external core 30 and internal core 31, make possible the preferential diffusion of the electrons emitted by the cores at the center of magnetic resonance cavities 33.

The gaseous medium already treated in the first chamber then penetrates the second chamber by passing through holes 29 in second plate 27 and penetrating second chamber 35.

Since cores 37 and 38 are connected to the positive potential and second plate 27 to the negative potential, the destruction and loss of molecular cohesion of the rest of the particles contained in the gaseous medium circulating in the sterilizer are ensured in second chamber 35.

Thus, second plate 27 constitutes an interface between first chamber 28 for disintegration of the biological structures and second chamber 35 for deterioration of the destructured particles.

These two chambers make possible the ionic sterilization of the gaseous medium loaded with microorganisms that circulates in the sterilizer, thanks to the emission of electrons accelerated by cores 30 and 31.

Reference is now made to FIG. 6, which illustrates a filter such as those represented by reference numbers 3 and 4 in FIG. 1.

This filter 6 has housing 60 which is intended to be traversed by a gaseous medium, penetrating through grill 61.

The gaseous medium penetrating filter 6 can be relatively moist. This is why means for recovering the water present in the gaseous medium are advantageously provided in housing 60. In the embodiment illustrated in FIG. 6, these means consist of a space with baffles 62; the water recovered can be evacuated by drain hole 63 provided in the bottom of the housing. Space 62 preferably has insulating covering 64.

Housing 60 is partially filled with a porous active material containing an oxidizing substance, an oxido-reducing substance, and an oxygen absorbing substance. This material bears reference number 65 in FIG. 6. It can be organized in granules or in plates.

The purpose of this active material is to purify the gaseous medium of the volatile organic compounds by redox filtration and ionic oxidation.

As an example, such a porous active material contains approximately 47 to 52 wt % of a silicon and carbon composite substance, approximately 12 to 20 wt % carbon, approximately 5 to 7 wt % hydroxyl, and approximately 1 to 2 wt % oxygen, its porosity being in particular between 60 and 85% by volume. The porosity represents the percentage of free space in the material.

This active material has a high specific surface area thanks to the presence of numerous pores whose dimensions are between 60 and 100 A.

The pores particularly make possible the adsorption of the gaseous medium which penetrates these pores, then the absorption of this gaseous medium in the course of which a reaction occurs between the volatile organic compounds of the gaseous medium and the material itself. This reaction makes possible the chemical conversion of the organic compounds into non-toxic gases, particularly $SO_2$ or $CO_2$.

The physicochemical sensitivity of the porous active material can be accentuated and regulated in terms of relative humidity and temperature thanks to plate 66, which can be placed in the middle of porous material 65. This plate 66 has windows 67 that are faced with platinum sponge, the perforated plate being nickel.

Plate 66 can be placed under an electrical potential of a few millivolts to a few volts, and its essential function is to promote chemical conversion of the volatile organic compounds that are to be purified.

Furthermore, as will be seen subsequently in the description, this plate 66 makes possible a supply of heat controlled as a function of the relative humidity of the enclosure from which the gaseous medium is extracted, and in particular the relative humidity of the storage chambers of a refrigerator.

Moreover, plate 66 preferably has electrical resistors 68. Their temperature function can be programmed manually or automatically in order to ensure recycling and regeneration of active material 65.

The gaseous medium treated by the active material then arrives in chamber 69 and circulates over electrodes 50 whose high potential electrostatic charge is supplied by electrical terminals 51.

The gaseous medium finally emerges from filter 6 through grill 52.

Thus, the gaseous medium, after passage through the filter according to the invention, is purified of the volatile organic compounds that it might contain. The conversion of these organic compounds leads to emission of gases such as $SO_2$ or $CO_2$ that generally are inhibitors with regard to development of microorganisms, which contributes to the effectiveness of the process according to the invention.

As indicated in the preceding, the device according to the invention essentially includes sterilizer 2. However, the presence of a filter at the site of suction of the gaseous medium from enclosure 1 and at the site of re-introduction of the gaseous medium into the enclosure, such as filters 3 and 4 represented in FIG. 1, makes it possible to destroy the volatile organic compounds as well as the odors released by the gaseous medium due particularly to the presence of aldehydes. On the other hand, the destruction of contaminating particles is essentially obtained by means of sterilizer 2.

The process and the device according to the invention can be applied in particular to treatment of gaseous media present in the chambers of refrigerators.

Thus, the invention also relates to a refrigerated apparatus, containing at least one storage chamber, associated with a treatment device according to the invention.

This refrigerated apparatus can also have at least two storage chambers, whose temperature and relative humidity will be adapted as a function of the preservation conditions for the food products placed in each of these chambers. Such a refrigerated apparatus therefore makes possible a differentiated treatment of the storage chambers, while guaranteeing sterilization and filtration of the gaseous media contained in each of these specialized chambers.

Reference is made to FIGS. 7 and 8, which illustrate a refrigerated apparatus according to the invention.

This refrigerator 7 has, in this example, two storage compartments 70 and 71, each of them being closed by, respectively, door 72, 73.

Each of these compartments 70 and 71 has some means for adapting the gaseous medium that it contains to the conditions of temperature, relative humidity and ventilation suitable for the type of preserved materials.

Thus, in this example, the temperature of the gaseous medium contained in compartment 71 will be regulated to between 3 and 7° C.

Compartment 70 in this example is intended for preserving meats and fish.

The temperature of this compartment 70 will be set at approximately 0° C. by temperature setting means 74, while the relative humidity will be regulated to between 40 and 80% by means of device 75, which in particular has at least one probe **75*a* for measuring humidity and at least one nozzle 75*b* for injecting water spray into compartment 70**.

As shown also by FIG. 8, in each of respective refrigerated compartments 70, 71, the gaseous medium present in the compartment is sucked in by the ventilation circuit which includes, respectively, first duct 700, 710, the suction being obtained by means of, respectively, fan 701, 711.

In each compartment, the air is sucked in, respectively, through at least one filter 702, 712. The filters are preferably placed in a side wall, the suction of course also occurring at this side wall.

Filters 702 and 712 have the characteristics that were described for filter 6 in reference to FIG. 6.

Thus, the gaseous medium circulating in first duct 700, 710 is already purified of at least a part of the volatile organic compounds that it might contain.

This gaseous medium then passes through, respectively, sterilizer 703, 713 for treating the most important part, the contaminating particles of the gaseous medium. Preferably, a voltage of 20,000 volts is applied to the sterilizer.

Tests that have been performed show that, by means of this sterilization, the deep anaerobic germs are blocked and the psychrotrophic germs responsible for surface alteration are greatly slowed down. This sterilization, which destroys practically all the microorganisms present in the gaseous medium, thus makes it possible to preserve the products present in each of the compartments with optimal quality.

The air leaving, respectively, each sterilizer 703, 713, is led through, respectively, second duct 704, 714 to second filter 705, 715 which is preferably placed, respectively, at the upper part of each compartment 70, 71. These second filters make it possible to further purify the gaseous medium treated by the sterilizer, particularly in order to convert the volatile organic compounds and to absorb the odors, before discharging the treated gaseous medium into each compartment.

In the embodiment illustrated in FIG. 8, storage compartment 70 has additional refrigeration circuit 706 for further cooling the gaseous medium that is re-introduced into compartment 70 via filter 705.

The process and the device according to the invention can have numerous applications other than the treatment of storage atmospheres, and can in particular be used for treating air circulating in air conditioning devices.

The invention claimed is:

1. A treatment process for a gaseous medium containing airborne contaminating biological structures, the process including:

generating a flow of accelerated electrons, interacting the electron flow and the gaseous medium, thereby causing breakdown or destruction of the biological structures by ionization and sterilization of the gaseous medium, and passing the gaseous medium through a plate with channels having a converging section and a diverging section so that the gaseous medium accelerates and converges toward the electron flow in a swirling stream before interaction with the electron flow.

2. The process according to claim 1, including generating a second electron flow interacting with the gaseous medium in which the contaminating particles have been broken down by ionization to transform the particles into a gas.

3. The process according to claim 1, including passing the gaseous medium through an active porous material and adsorbing the gaseous medium which penetrates pores of the porous material, and producing a chemical reaction between volatile organic compounds in the gaseous medium and the porous material, transforming the volatile organic compounds into non-toxic gases.

4. The process according to claim 3, including recovering water from the gaseous medium before passing the gaseous medium through the porous material.

5. The process according to claim 1, including suctioning the gaseous medium from an enclosure and delivering the gaseous medium, after treatment, back to the enclosure.

6. The process according to claim 1, wherein the channels are on axes, and the axes of the channels converge toward a source of electrons.

7. A device for treatment of a gaseous medium containing contaminating particles, the device including a sterilizer having:
an envelope within which a gaseous medium circulates, having a first opening for entrance of the gaseous medium and a second opening for exit of the gaseous medium after treatment, and
first and second electrically conductive plates defining a first chamber in the envelope, the first plate being attached at the first opening, being connected to the positive potential of an electrical power supply, and perforated with channels to accelerate the gaseous medium, the second plate supporting first and second spaced apart cores in the first chamber and emitting electrons, the second plate being connected to the negative potential of the electrical power supply, the first core having a smaller diameter than the second core and being farther from the first plate than the second core, the channels of the first plate having a converging section and a diverging section with axes converging toward a center of the first core and distributed to create a peripheral turbulence so that the gaseous medium circulates in a swirling stream that converges toward the center of the first core.

8. The device according to claim 7, comprising vanes which extend toward the first chamber and are in electrical contact with the first plate, defining magnetic resonance cavities.

9. The device according to claim 7, wherein the second plate is perforated with holes and defines, with a third plate, a second chamber within the envelope, the second plate supporting at least one electrode extending in the second chamber, the third plate being attached at the second opening of the envelope and supporting a third core extending in the second chamber toward the electrode, the third plate being electrically conductive and connected to the positive potential of the electrical power supply and having holes to evacuate the gaseous medium from the envelope of the sterilizer.

10. The device according to claim 9, in which the electrode borne by the second plate is cylindrical and has peripheral vanes defining magnetic resonance cavities.

11. The device according to claim 7, including at least one filter traversed by the gaseous medium, and having a housing filled at least partially with a porous active material containing an oxidizing substance, an oxido-reducing substance, and an oxygen absorbing substance, for conversion of volatile organic compounds into a non-toxic gas.

12. The device according to claim 11, wherein the active material in the filter contains approximately 47 to 52 wt % of a silicon and carbon composite substance, approximately 12 to 20 wt % carbon, approximately 5 to 7 wt % hydroxyl, and approximately 1 to 2 wt % oxygen, and has a porosity between 60 and 85% by volume.

13. The device according to claim 11, wherein the filter contains a nickel plate inside the porous active material, and having windows faced with a platinum sponge.

14. The device according to claim 11, including means for recovering water from the gaseous medium and located at an entrance of the filter.

15. The device according to claim 11, wherein the nickel plate includes electrical resistors that change in temperature to recycle and regenerate the active material.

16. A refrigerated apparatus including at least one storage compartment including a treatment device according to claim 7 and including means for setting the temperature, relative humidity, and ventilation for products intended to be placed in the compartment.

17. The refrigerated apparatus according to claim 16, in which the treatment device includes first and second filters, the first filter being located at an entrance of a ventilation circuit which sucks in the gaseous medium from the storage compartment and delivers the gaseous medium to the sterilizer, and the second filter being located at an outlet of the ventilation circuit and receiving the gaseous medium treated by the sterilizer to deliver the gaseous medium, after filtering, to the storage compartment.

\* \* \* \* \*